United States Patent [19]

Chao et al.

[11] Patent Number: 5,381,233
[45] Date of Patent: Jan. 10, 1995

[54] POLARIZED-LIGHT SCATTEROMETER FOR MEASURING THE THICKNESS OF A FILM COATED ON THE PARTIAL OF A SUBSTRATE

[75] Inventors: Shiuh Chao; Jyh-Shin Chen, both of Taipei; Tsai-Chu Hsiao, Chung-Li, all of Taiwan, Prov. of China

[73] Assignee: National Tsing Hua University, Hsinchu, Taiwan, Prov. of China

[21] Appl. No.: 25,854

[22] Filed: Mar. 3, 1993

[51] Int. Cl.$^6$ ............................ G01J 4/00; G01J 4/04
[52] U.S. Cl. ................................ 356/369; 356/364; 356/381
[58] Field of Search ................ 356/369, 364, 381, 382

[56] References Cited

U.S. PATENT DOCUMENTS

| | | | |
|---|---|---|---|
| 4,838,695 | 6/1989 | Mansuripur et al. | 356/369 |
| 4,983,823 | 1/1991 | Isobe | 356/369 |
| 5,108,185 | 4/1992 | Mansuripur et al. | 356/369 |
| 5,191,387 | 3/1993 | Ichikawa et al. | 356/364 |

FOREIGN PATENT DOCUMENTS 0012404  7/1992  European Pat. Off. ............ 356/369

OTHER PUBLICATIONS

Bickel et al., "Stakes vectors, Muello matrices, and polarized scattered light", American Journal of Physics, vol. 53, No. 5, May 1985, pp. 468–479.

Primary Examiner—Rolf Hille
Assistant Examiner—Alexander Oscar Williams
Attorney, Agent, or Firm—Marshall & Melhorn

[57] ABSTRACT

A polarized-light scatterometer for measuring the thickness of a film coated on the partial of a substrate, the film having a straight line edge on the surface of the substrate coated with the film. The polarized-light scatterometer is composed of means for generating an incident beam (a fixed polarization state input beam) striking the straight line edge of the film; means for detecting the intensity of a scattered beam which is scattered by the incident beam within a predetermined angular range; means for rotating the detecting means about the Z-axis within the predetermined angular range; means for adjusting the intensity of the scattered beam; means for obtaining the Mueller matrix by using the Bickel-Bailey method; means for normalizing all the elements of the Mueller matrix; means for recording the corresponding scattered angle of the scattered beam having maximum intensity variation; means for obtaining the relation diagrams between the normalized elements and the thickness of the film respectively, and all the relation diagrams are obtained under the scattered angle having maximum intensity variation; means for choosing the relation diagrams that the normalized elements have greater sensitivity to the thickness of the film; means for obtaining the values of normalized elements of an unknown thickness of the same film; means for obtaining the thicknesses of the film of unknown thickness corresponding to the relation diagrams by using the values of the normalized elements; and means for determining the thickness of the unknown thickness film by choosing common thickness among the relation diagrams.

2 Claims, 8 Drawing Sheets

| $S_{11}$ ✴ | $S_{12}$ → ✴ | $S_{13}$ ✴ | $S_{14}$ ◯ ✴ |
|---|---|---|---|
| ✴ ✴ $S_{11}$ | ✴ $S_{11}+S_{12}$<br>✴ $S_{11}-S_{12}$ | ✴ $S_{11}+S_{13}$<br>✴ $S_{11}-S_{13}$ | ✴ ✴ $S_{11}+S_{14}$<br>◯ ◯ $S_{11}-S_{14}$ |
| $S_{21}$ ↔ | $S_{22}$ ↔ | $S_{22}$ ↔ | $S_{24}$ ◯ |
| ✴ $S_{11}+S_{21}$<br>✴ $S_{11}-S_{21}$ | ↔ $S_{11}+S_{12}+S_{21}+S_{22}$<br>↔ $S_{11}-S_{12}-S_{21}-S_{22}$<br>↔ $S_{11}+S_{12}-S_{21}-S_{22}$<br>↔ $S_{11}-S_{12}+S_{21}+S_{22}$ | ↔ $S_{11}+S_{13}+S_{21}+S_{22}$<br>↔ $S_{11}-S_{13}-S_{21}-S_{22}$<br>↔ $S_{11}+S_{13}-S_{21}-S_{22}$<br>↔ $S_{11}-S_{13}+S_{21}+S_{22}$ | ◯ → $S_{11}+S_{14}+S_{21}+S_{24}$<br>◯ → $S_{11}-S_{14}-S_{21}-S_{24}$<br>◯ → $S_{11}+S_{14}-S_{21}-S_{24}$<br>◯ → $S_{11}-S_{14}+S_{21}+S_{24}$ |
| $S_{31}$ ✴ | $S_{22}$ ↔ | $S_{33}$ | $S_{34}$ ◯ |
| ✴ $S_{11}+S_{31}$<br>✴ $S_{11}-S_{31}$ | ↔ $S_{11}+S_{12}+S_{31}+S_{32}$<br>↔ $S_{11}+S_{12}-S_{31}-S_{32}$<br>↔ $S_{11}-S_{12}+S_{31}+S_{32}$<br>↔ $S_{11}-S_{12}-S_{31}+S_{32}$ | $S_{11}+S_{13}+S_{31}+S_{33}$<br>$S_{11}+S_{13}-S_{31}-S_{33}$<br>$S_{11}-S_{13}+S_{31}-S_{33}$<br>$S_{11}-S_{13}-S_{31}+S_{33}$ | ◯ $S_{11}+S_{14}+S_{31}+S_{34}$<br>◯ $S_{11}-S_{14}-S_{31}-S_{34}$<br>◯ $S_{11}+S_{14}-S_{31}+S_{34}$<br>◯ $S_{11}-S_{14}+S_{31}+S_{34}$ |
| $S_{41}$ ✴ ◯ | $S_{42}$ ◯ | $S_{43}$ ◯ | $S_{44}$ ◯ |
| ◯ $S_{11}+S_{41}$<br>◯ $S_{11}-S_{41}$ | → ◯ $S_{11}+S_{12}+S_{41}+S_{42}$<br>→ ◯ $S_{11}-S_{12}-S_{41}-S_{42}$<br>→ ◯ $S_{11}+S_{12}-S_{41}+S_{42}$<br>→ ◯ $S_{11}-S_{12}-S_{41}+S_{42}$ | ◯ $S_{11}+S_{13}+S_{41}+S_{43}$<br>◯ $S_{11}-S_{13}-S_{41}-S_{43}$<br>◯ $S_{11}+S_{13}-S_{41}+S_{43}$<br>◯ $S_{11}-S_{13}+S_{41}+S_{43}$ | ◯ ◯ $S_{11}+S_{14}+S_{41}+S_{44}$<br>◯ ◯ $S_{11}-S_{14}-S_{41}-S_{44}$<br>◯ ◯ $S_{11}+S_{14}-S_{41}-S_{44}$<br>◯ ◯ $S_{11}-S_{14}+S_{41}+S_{44}$ |

FIG. 3

POLARIZED-LIGHT SCATTEROMETER FOR MEASURING THE THICKNESS OF A FILM COATED ON THE PARTIAL OF A SUBSTRATE

BACKGROUND OF THE INVENTION

The present invention relates to a polarized-light scatterometer, and in particular to a polarized-light scatterometer that is capable of measuring the thickness of a film coated on the partial of a substrate.

There are a lot of methods for measuring the thickness of a film, such as using an ellipsometer or a transmission spectrum. However, both of them are poor at measuring the thickness of non-transparent film. If the thickness of a film is measured by the eddy-current method or the electrical resistance method, then a substrate material that is not-conducting and not-magnetic must be employed.

In addition, when the stylus method is used to measure the thickness of a film coated on the partial of a substrate, the film may be scraped by the stylus during the measurement, affecting the precision of the measurement.

SUMMARY OF THE INVENTION

It is an object of the present invention to provide a polarized-light scatterometer that is capable of measuring the thickness of a film coated on the partial of a substrate.

It is another object of the present invention to provide a method that uses a polarized-light scatterometer to measure the thickness of a film coated on the partial of a substrate.

In accordance with the objects of the present invention, a polarized-light scatterometer for measuring the thickness of a film coated on the partial of a substrate, comprising: (a) means for locating the origin of a X,Y,Z-coordinate on the surface of the substrate coated with the film, the normal direction of the surface of the substrate coated with the film is defined as the X-axis, the direction parallel to the surface of the substrate coated with the film is defined as the Y-axis, the film having a straight line edge on the Z-axis of the surface of the substrate coated with the film; (b) means for generating a fixed polarization state input beam striking the straight line edge of the film, the path of the fixed polarization state input beam being on the X-Y plane; (c) means for detecting the intensity of a fixed polarization state beam scattered by the fixed polarization state input beam striking the straight line edge of the film within a predetermined angular range; (d) means for rotating the detecting means about the Z-axis within the predetermined angular range; (e) means for adjusting the relative intensity of the fixed polarization state input beam and the fixed polarization state beam scattered by the fixed polarization state input beam striking the straight line edge of the film; (f) means for obtaining a 4×4 matrix, S, that can transfer a 4×1 matrix, $S_i$, that represents the polarization state of the fixed polarization state input beam to a 4×1 matrix, $S_s$, that represents the polarization state of the fixed polarization state beam scattered by the fixed polarization state input beam striking the straight line edge of the film by using the Bickel-Bailey method, that is $$S_s = S \cdot S_i$$

where the dot,".", represents multiplication, the 4×4 matrix, S, is named as "Mueller matrix" and is defined to be $$S = \begin{bmatrix} s_{11} & s_{12} & s_{13} & s_{14} \\ s_{21} & s_{22} & s_{23} & s_{24} \\ s_{31} & s_{32} & s_{33} & s_{34} \\ s_{41} & s_{42} & s_{43} & s_{44} \end{bmatrix};$$

(g) means for normalizing all the elements of the Mueller matrix, the normalized elements, $s_{ij}^*$, is defined as $$s_{ij}^* = \frac{s_{ij}}{s_{11}}, i = 1 \text{ to } 4, j = 1 \text{ to } 4;$$

(h) means for recording the corresponding scatter angle of the fixed polarization state beam scattered by the fixed polarization state input beam striking the straight line edge of the film having maximum intensity variation ; (i) means for obtaining the relation diagrams between the normalized elements, $s_{12}^*$, $s_{21}^*$, $s_{22}^*$, $s_{33}^*$, $s_{34}^*$, $s_{43}^*$, $s_{44}^*$ and the thicknesses of the film respectively by repeating the step (a) to the step (g) with different predetermined thicknesses of the film, and all the relation diagrams are obtained under the corresponding scatter angle of the fixed polarization state beam scattered by the fixed polarization state input beam striking the straight line edge of the film having maximum intensity variation; (j) means for choosing the relation diagrams in the step (i) that the normalized elements, $s_{12}^*$, $s_{21}^*$, $s_{22}^*$, $s_{33}^*$, $s_{34}^*$, $s_{43}^*$, $s_{44}^*$ have greater sensitivity to the thickness of the film; (k) means for repeating the step (a) to the step (g) with an unknown thickness of the film, and obtaining the values of normalized elements, $s_{12}^*$, $s_{21}^*$, $s_{22}^*$, $s_{33}^*$, $s_{34}^*$, $s_{43}^*$, $s_{44}^*$ of the film of unknown thickness; (l) means for obtaining the thicknesses of the film of unknown thickness from the relation diagrams obtained in the step (j) corresponding to the relation diagrams by using the values of the normalized elements, $s_{12}^*$, $s_{21}^*$, $s_{22}^*$, $s_{33}^*$, $s_{34}^*$, $s_{43}^*$, $s_{44}^*$ in the step (k) respectively; and (m) means for determining the thickness of the film of unknown thickness by choosing the common thickness among the relation diagrams in the step (l). A method for measuring the thickness of a film coated on a partial portion of a substrate, comprising the following steps of: (a) locating the origin of a X,Y,Z-coordinate on the surface of the substrate coated with the film, the normal direction of the surface of the substrate coated with the film is defined as the X-axis, the direction parallel to the surface of the substrate coated with the film is defined as the Y-axis, the film having a straight line edge on the Z-axis of the surface of the substrate coated with the film; (b) generating a fixed polarization state input beam striking the straight line edge of the film, the path of the fixed polarization state input beam being on the X-Y plane; (c) detecting the intensity of a fixed polarization state beam scattered by the fixed polarization state input beam striking the straight line edge of the film within a predetermined angular range; (d) adjusting the relative intensity of said fixed polarization state input beam and said fixed polarization state input beam and the fixed polarization state beam scattered by the fixed polarization state input beam striking the straight line edge of the film; (e) obtaining a 4×4 matrix, S, that can transfer a 4×1 matrix, $S_i$, that represents the polarization state of the fixed polarization state input beam to a 4×1 matrix, $S_s$, that represents the polarization state of the fixed polarization state beam scattered by the fixed polarization state input beam striking the straight line edge of the film by using the Bickel-Bailey method, that is $$S_s = S \cdot S_i$$

where the dot, "·", represents multiplication, the 4×4 matrix, S, is named as "Mueller matrix" and is defined to be $$S = \begin{bmatrix} s_{11} & s_{12} & s_{13} & s_{14} \\ s_{21} & s_{22} & s_{23} & s_{24} \\ s_{31} & s_{32} & s_{33} & s_{34} \\ s_{41} & s_{42} & s_{43} & s_{44} \end{bmatrix};$$

(f) normalizing all the elements of the Mueller matrix, the normalized elements, $s_{ij}^*$, is defined as $$s_{ij}^* = \frac{s_{ij}}{s_{11}}, \ i = 1 \text{ to } 4, j = 1 \text{ to } 4;$$

(g) recording the corresponding scatter angle of the fixed polarization state beam scattered by the fixed polarization state input beam striking the straight line edge of the film having maximum intensity variation; (h) obtaining the relation diagrams between the normalized elements, $s_{12}^*$, $s_{21}^*$, $s_{22}^*$, $s_{33}^*$, $s_{34}^*$, $s_{43}^*$, $s_{44}^*$ and the thickness of the film respectively by repeating the step (a) to the step (f) with different predetermined thicknesses of the film, and all the relation diagrams are obtained under the corresponding scattered angle of the fixed polarization state beam scattered by the fixed polarization state input beam striking the straight line edge of the film having maximum intensity variation; (i) choosing the relation diagrams in the step (h) that the normalized elements, $s_{12}^*$, $s_{21}^*$, $s_{22}^*$, $s_{33}^*$, $s_{34}^*$, $s_{43}^*$, $s_{44}^*$ have greater sensitivity to the thickness of the film; (j) repeating the step (a) to the step (f) with an unknown thickness of the film, and obtaining the values of normalized elements, $s_{12}^*$, $s_{21}^*$, $s_{22}^*$, $s_{33}^*$, $s_{34}^*$, $s_{43}^*$, $s_{44}^*$ of the film of unknown thickness; (k) obtaining the thicknesses of the film of unknown thickness from the relation diagrams obtained in the step (i) corresponding to the relation diagrams by using the values of the normalized elements, $s_{12}^*$, $s_{21}^*$, $s_{22}^*$, $s_{33}^*$, $s_{34}^*$, $s_{43}^*$, $s_{44}^*$ in the step (j) respectively; and (l) determining the thickness of the film of unknown thickness by choosing the common thickness among the relation diagrams in the step (k).

BRIEF DESCRIPTION OF THE DRAWINGS

The present invention can be more fully understood by reference to the following description and accompanying drawings, wherein:

FIG. 3 is a matrix array of the Bickel-Bailey method showing the matrix element combination measured for various arrangements of input and output optical elements (random, linear, and circular polarizations);

DETAILED DESCRIPTION THE PREFERRED EMBODIMENTS

The Mueller Matrices and Stokes Vectors

Figure 1:
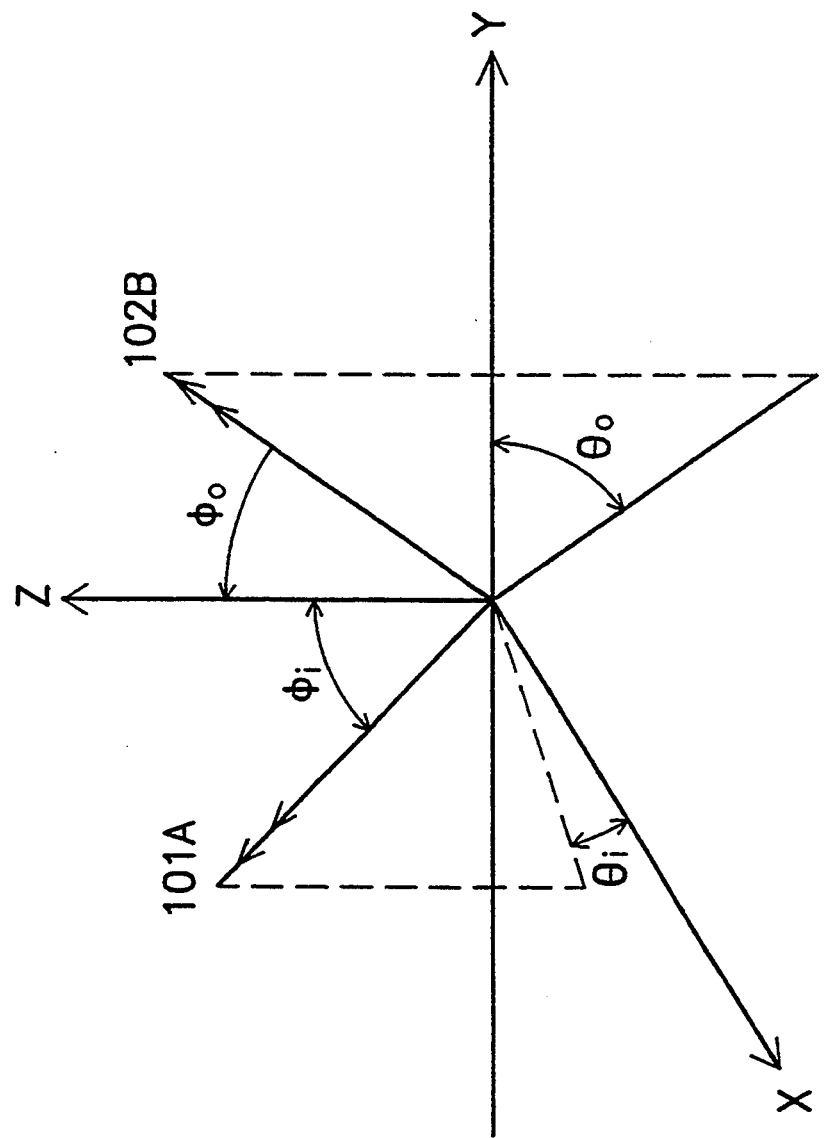
FIG. 1 is an schematic diagram of an incident beam (a fixed polarization state input beam) and a scattered beam (a fixed polarization state beam scattered by the fixed polarization state input beam that strikes the straight line edge of the film) on a X,Y,Z-coordinate.

Referring to FIG. 1, there is shown an schematic diagram of an incident beam (a fixed polarization state input beam) and a scattered beam (a fixed polarization state beam scattered by the fixed polarization state input beam that strikes the straight line edge of the film) on a X,Y,Z-coordinate, where 101A indicates the incident beam, $\Theta_i$ indicates the incident angle, $\phi_i$ indicates the incident angle, 102B indicates the scattered beam, $\Theta_o$ indicates the scattering angle, $\phi_o$ indicates the scattering angle.

The polarization state of the incident beam can be represented by a "4×1" matrix under the X, Y, Z-coordinate, $$S_i = \begin{bmatrix} s_{1i} \\ s_{2i} \\ s_{3i} \\ s_{4i} \end{bmatrix}$$

The polarization state of the scattered beam can also be represented by a "4×1" matrix under the X, Y, Z-coordinate, $$S_s = \begin{bmatrix} s_{1s} \\ s_{2s} \\ s_{3s} \\ s_{4s} \end{bmatrix}$$

The 4×1 matrix, $S_i$, can be transferred to the 4×1 matrix, $S_s$, by a 4×4 matrix, S, that is, $$S_s = S \cdot S_i$$

where the dot, "·", represents multiplication, the 4×1 matrix, $S_i$, and the 4×1 matrix, $S_s$, are named as Stokes vectors, the 4×4 matrix, S, is named as a Mueller matrix and is defined to be $$S = \begin{bmatrix} s_{11} & s_{12} & s_{13} & s_{14} \\ s_{21} & s_{22} & s_{23} & s_{24} \\ s_{31} & s_{32} & s_{33} & s_{34} \\ s_{41} & s_{42} & s_{43} & s_{44} \end{bmatrix}$$

The Mueller matrix, S, has a close relationship between the optical properties and the geometrical structure of a scatterer. Among the sixteen elements of the Mueller matrix, S, some of them are very sensitive to the geometrical structure of the scatterer (for example, thickness), these elements can be obtained by an experimental method, and can also be used to measure thickness. If the scatterer possesses mirror symmetry about X-Y plane, then the matrix elements $s_{13}$, $s_{14}$, $s_{23}$, $s_{24}$, $s_{31}$, $s_{32}$, $s_{41}$ and $s_{42}$ are zero. The scatterer in FIG. 4 possesses mirror symmetry about X-Y plane.

The Bickel-Bailey Method to Obtain the Elements of a Mueller Matrix

The elements of the Mueller matrix can be obtained by the Bickel-Bailey method (refer to Am. J. Phys., Vol. 53, No. 5, May 1985).

Figure 2:
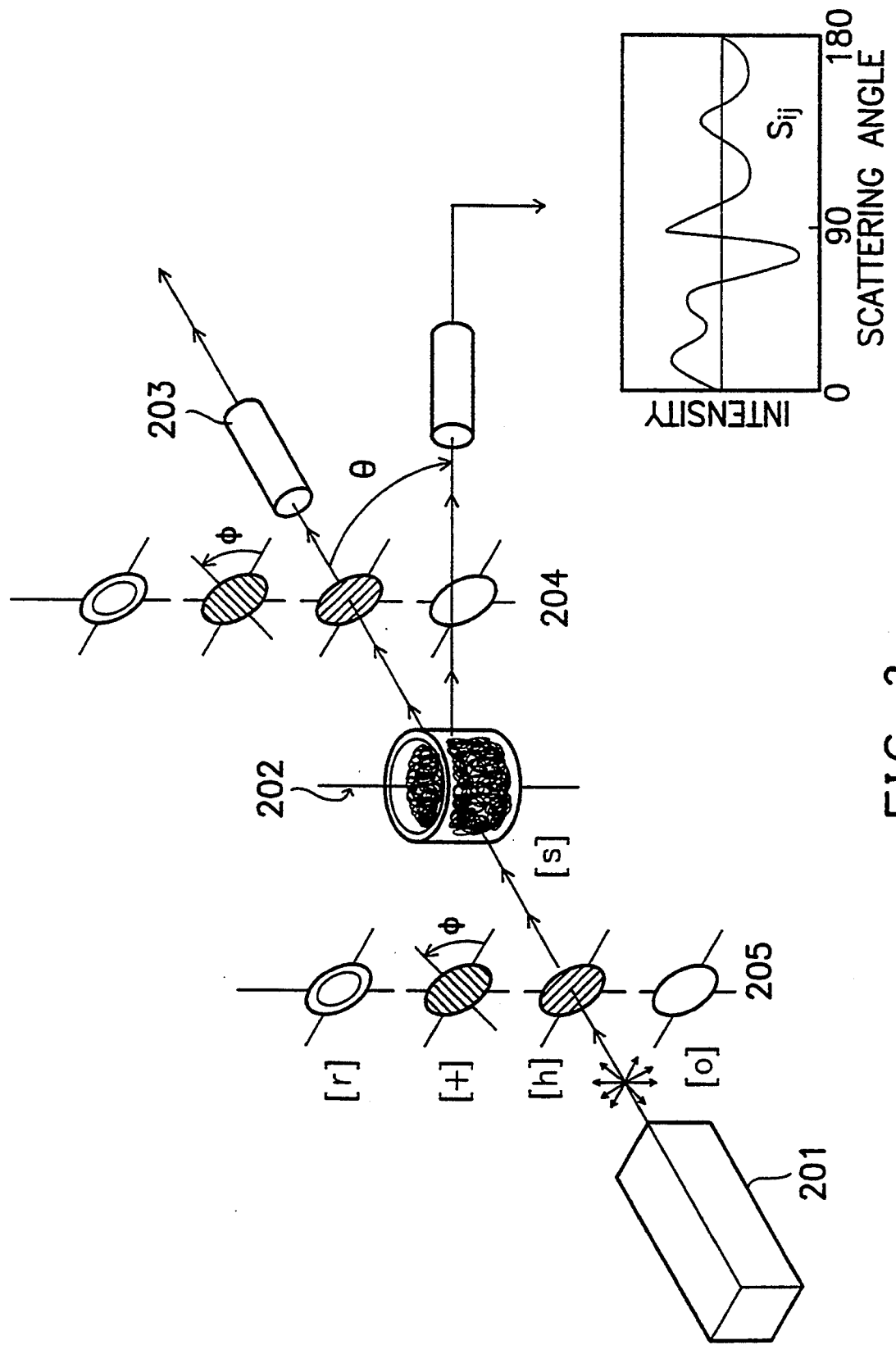
FIG. 2 is the experimental optical system of the Bickel-Bailey method used to measure all elements of the scattering matrix and polarization states.

FIG. 2 is the experimental optical system of the Bickel-Bailey method used to measure all elements of the scattering matrix and polarization states, where,

[r] indicates the right-hand circular polarization and its sign is " $\bigcirc$ ".

[+] indicates the +45° linear polarization and its sign is "$/$".

[h] indicates the horizontal linear polarization and its sign is "$\rightleftarrows$".

[o] indicates the random polarization and its sign is "$*$".

[s] indicates the scatterer.
201 indicates the Laser.
202 indicates the axis.
203 indicates the detector.
204 indicates the exit optics.
205 indicates the input optics.

The range of the detecting angle (scattering angle) is from 0° to 180°, and the detector can be moved from 0° to 180°, measuring the intensity of light at every angle.

The forty nine combinations are combined by the seven kinds of the polarizations before the scatterer, [s], and the seven kinds of the polarizes after the scatterer, [s], and these forty nine combinations can be used to obtain the sixteen elements of the Mueller matrix, as shown in FIG. 3.

Referring to FIG. 3, take $s_{22}\rightleftarrows\rightleftarrows$ as an example, the first $\rightleftarrows$ indicates the polarization state of the incident light, namely, adjusting the input optics, such that the polarization state of the incident light is horizontal linear polarization. The second $\rightleftarrows$ indicates the polarization state of the scattered light to be detected, namely, adjusting the exit optics, such that the horizontal linear polarization portion of the scattered light can pass through the exit optics and reach to the detector. There are four linear polarizations combinations in the box $s_{22}$, that is $\rightleftarrows\rightleftarrows$, $\rightleftarrows \updownarrow$, $\updownarrow \rightleftarrows$, $\updownarrow \updownarrow$. The value of the four corresponding light intensity can be read from the detector, that is $I_1$, $I_2$, $I_3$ and $I_4$. A four simultaneous equations can be obtained as follows, $$\begin{bmatrix} s_{11} + s_{12} + s_{21} + s_{22} = I_1 \\ s_{11} + s_{12} - s_{21} - s_{22} = I_2 \\ s_{11} - s_{12} + s_{21} - s_{22} = I_3 \\ s_{11} - s_{12} - s_{21} + s_{22} = I_4 \end{bmatrix}$$

and then the four unknown $s_{11}$, $s_{12}$, $s_{21}$, $s_{22}$ can be solved.

Similarly, the value of the elements, $s_{23}$, $s_{24}$, $s_{32}$, $s_{33}$, $s_{34}$, $s_{42}$, $s_{43}$, $s_{44}$ can also be solved. Consequently, all the elements of the Mueller matrix can be obtained.

Figure 4:
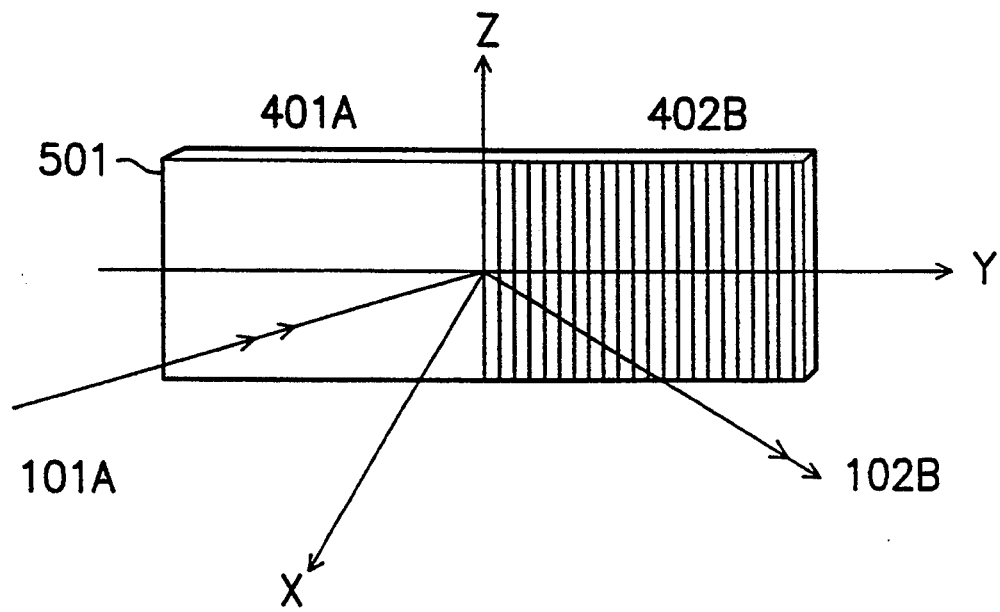
FIG. 4 is a front view of a schematic diagram of a scattered beam scattered by the incident beam that strikes the straight line edge of a film coated on the partial of a substrate.

Referring to FIG. 4, where 101A indicates the incident beam (a fixed polarization state input beam), 102B indicates the scattered beam (a fixed polarization state beam scattered by the fixed polarization state input beam that strikes the straight line edge of the film), 401A indicates the uncoated side, 402B indicates the coated side, 501 indicates the substrate, the normal direction of the surface of the substrate coated with the film is defined as the X-axis, the direction parallels to the surface of the substrate coated with the film is defined as the Y-axis, the film having a straight line edge on the Z-axis of the surface of the substrate coated with the film. Since both of the path of the incident beam and the path of the scattered beam are on the X-Y plane, there are only eight nonzero elements in the Mueller matrix, that is, $$S = \begin{bmatrix} s_{11} & s_{12} & 0 & 0 \\ s_{21} & s_{22} & 0 & 0 \\ 0 & 0 & s_{33} & s_{34} \\ 0 & 0 & s_{43} & s_{44} \end{bmatrix}$$

The present invention uses the Bickel-Bailey method to measure the elements of the Mueller matrix.

EXAMPLE

Figure 5:
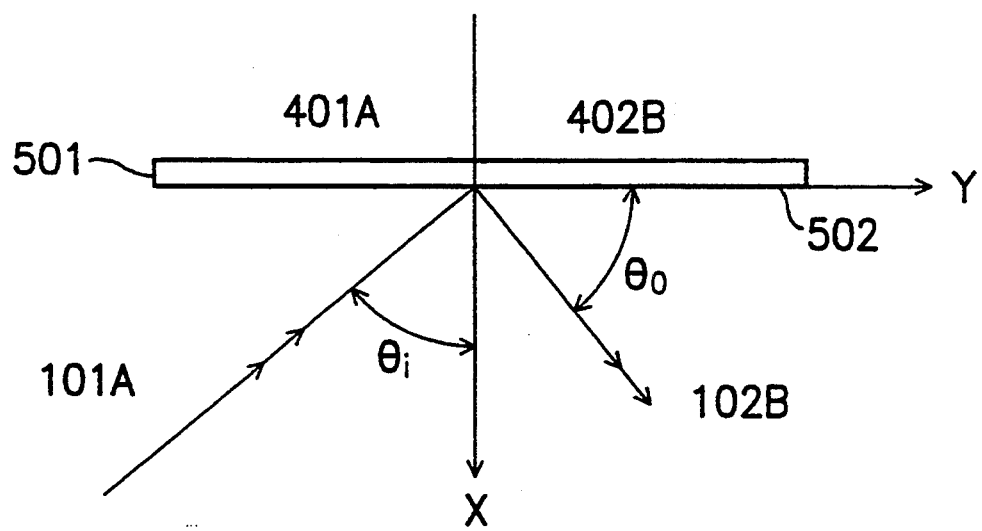
FIG. 5 is a top view of a schematic diagram of the incident beam that strikes the straight line edge of a film coated on the partial of a substrate and the path of the incident beam being on the X-Y plane.

Take $SiO_x$ film as an example, the $SiO_x$ is deposited in a high vacuum (about $10^{-5}$ Torr) oxygen, and form a film on a Silicon (Si) chip by a electron beam evaporation method, its refraction coefficient is about 1.5, i.e., nearly the same refraction coefficient as the $SiO_2$, thus it is named as $SiO_x$ film. The $SiO_x$ film is coated on the substrate, as shown in FIG. 5, where 101A indicates the incident beam (a fixed polarization state input beam), 102B indicates the scattered beam (a fixed polarization state beam scattered by the fixed polarization state input beam striking the straight line edge of the film), 401A indicates the uncoated side, 402B indicates the coated side, 501 indicates the substrate, 502 indicates the film, $\Theta_i$ indicates the incident angle, $\Theta_o$ indicates the detecting angle (scattering angle).

Figure 6:
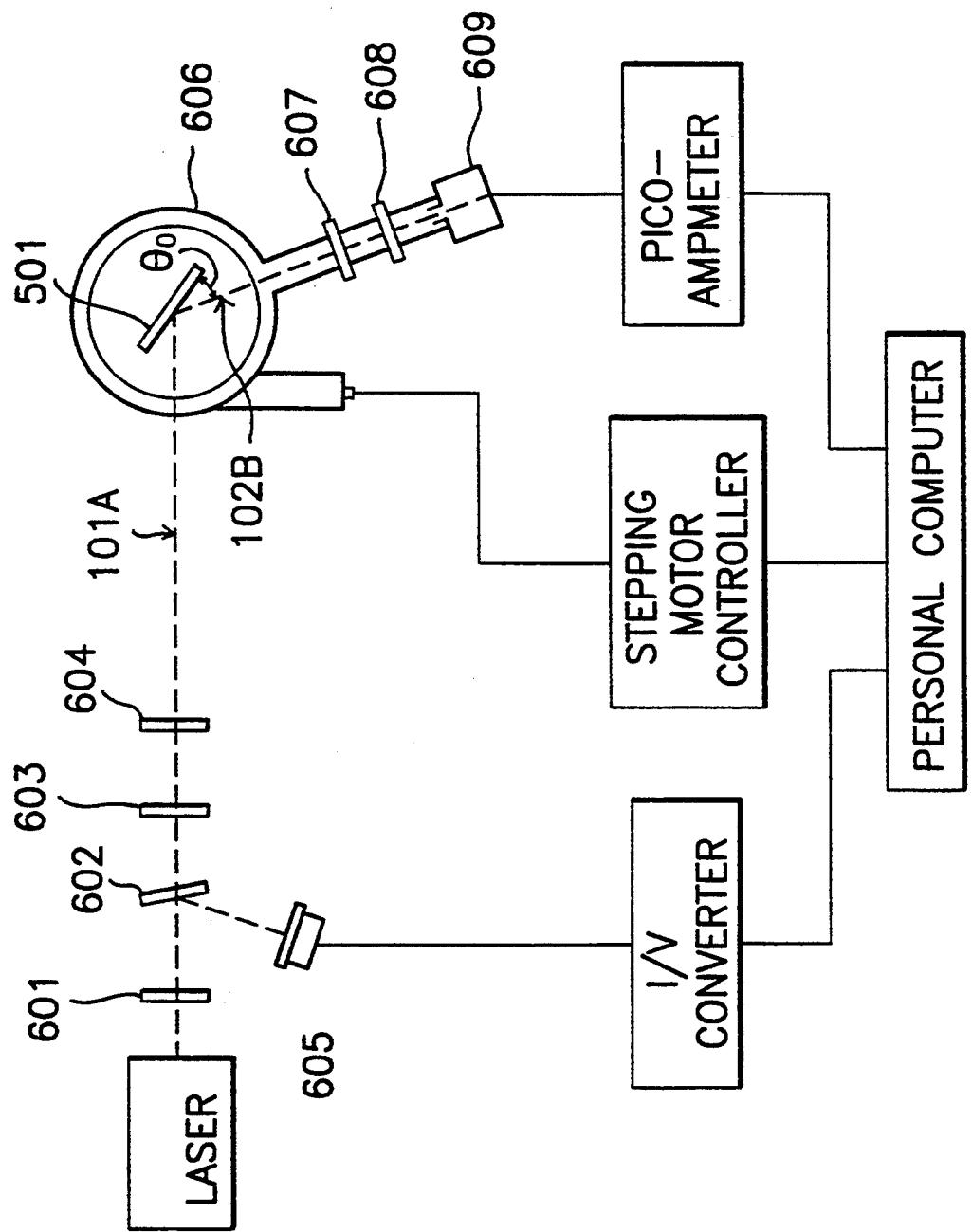
FIG. 6 is a measurement device diagram of the present invention.

The measurement device diagram of the present invention is shown in FIG. 6, where the source of the incident beam is a He—Ne Laser, 101A indicates the incident beam, 102B indicates the scattered beam, 501 indicates the substrate, 601, 603 and 608 indicates the linear polarized mirrors, 604 and 607 indicates the phase delay plates, 602 indicates the beam splitter, 609 indicates the photo-multiplier tube (PMT) for detecting the intensity of the scattered beam, 605 indicates the PIN photo-detector for detecting the drifting of the output power of the Laser, 606 indicates the rotation stage.

The phase delay plate 607, the linear polarized mirror 608 and the photo-multiplier tube (PMT) 609 are named as a polarized light detector. The signal of the PIN photo-detector is transmitted to a computer for adjusting the reading of the photo-multiplier tube (PMT). At the same time, a stepping motor controller is used for adjusting the detecting angle (scattering angle), $\Theta_o$.

Figure 7:
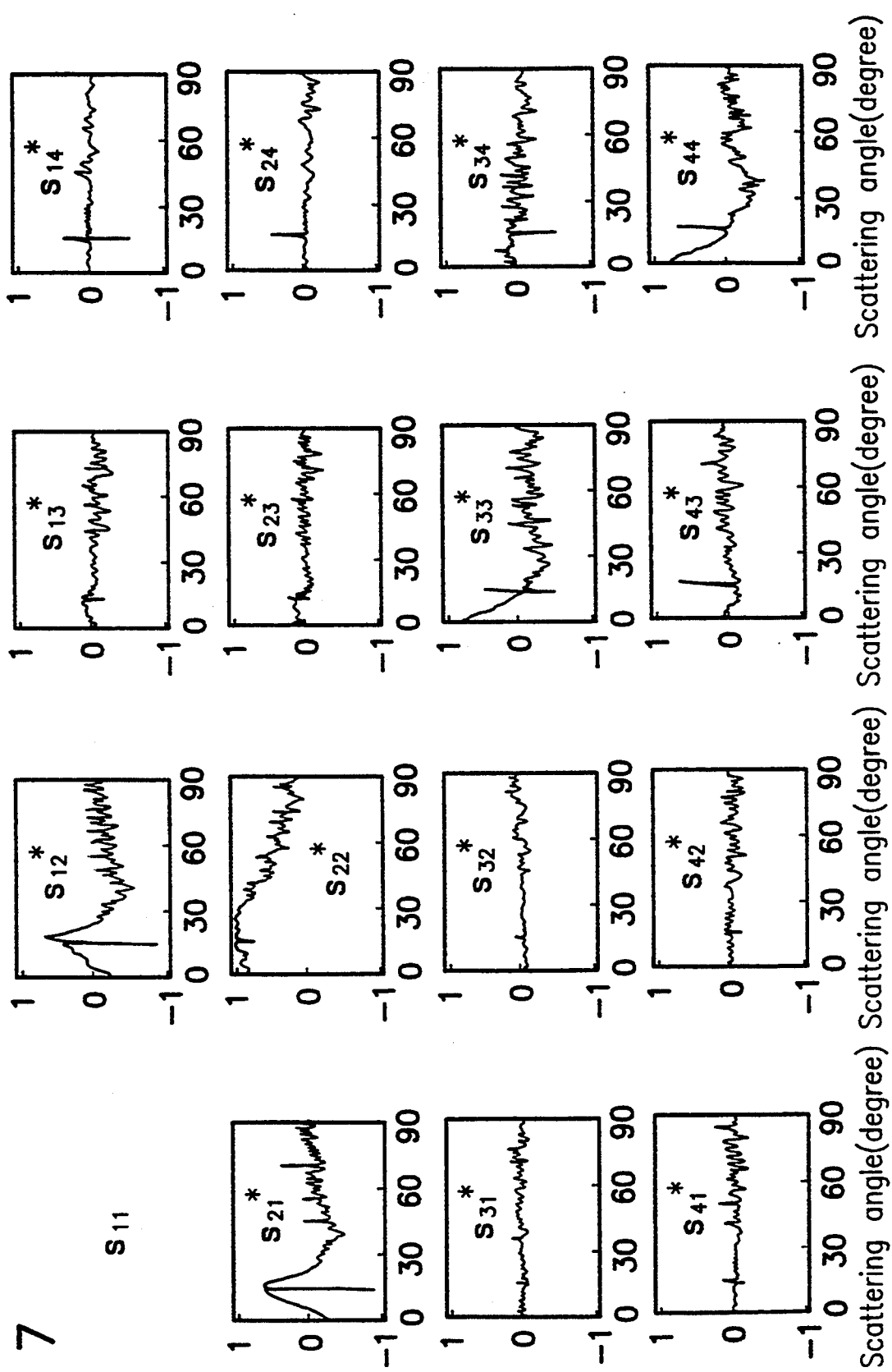
FIG. 7 depicts all the scattering intensity diagrams of the 84.1 nm thickness of a $SiO_x$ film.

Choose the Normalized Elements Having Greater Sensitivity to the Thickness of the Film and the Scattered Angle of the Scattered Beam Having Maximum Intensity Variation FIG. 7 depicts all the scattering intensity diagrams of the 84.1 nm thickness of a $SiO_x$ film.

Figure 8:
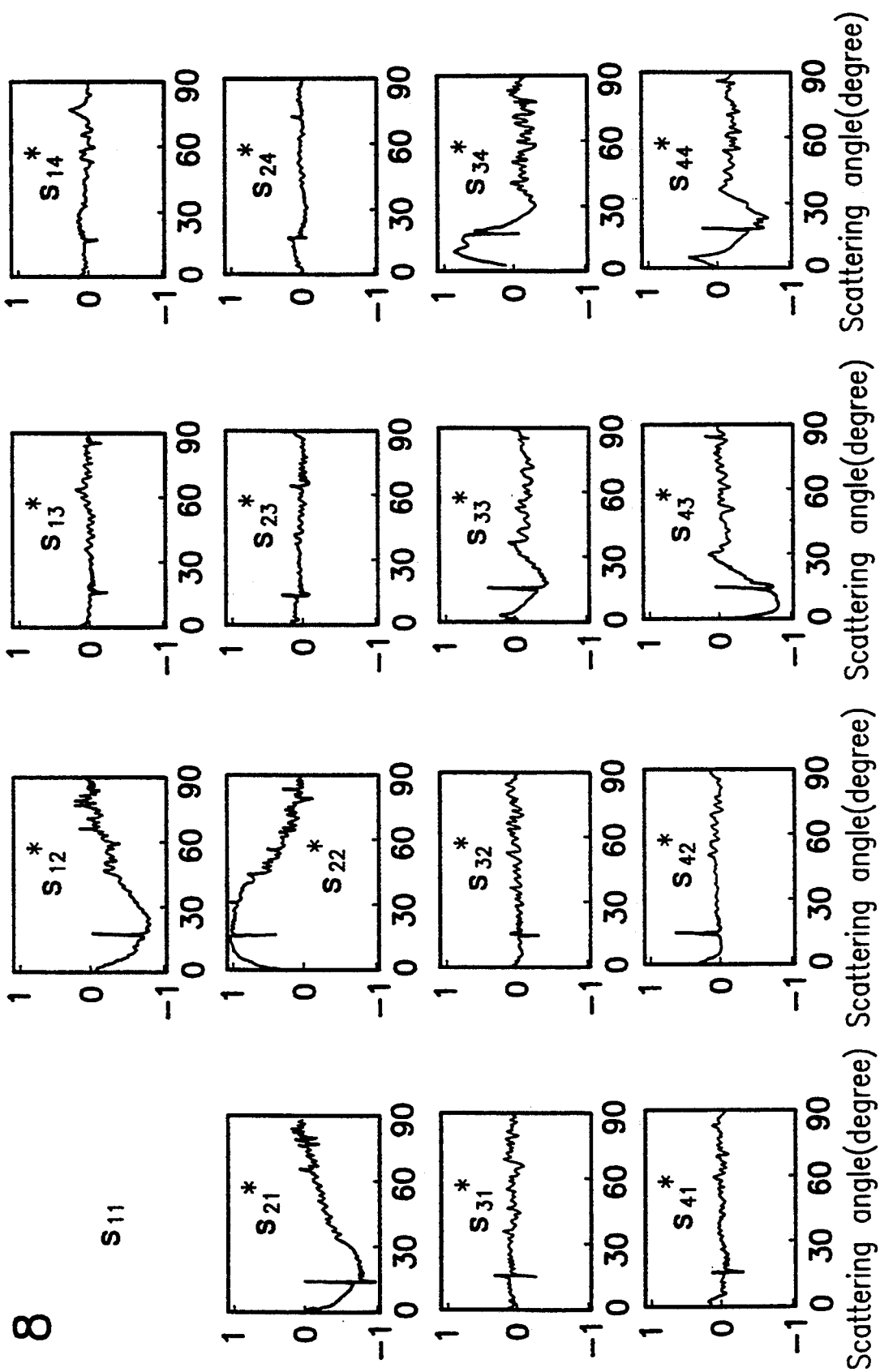
FIG. 8 depicts all the scattering intensity diagrams of the 336.4 nm thickness of a $SiO_x$ film.

FIG. 8 depicts all the scattering intensity diagrams of the 336.4 nm thickness of a $SiO_x$ film.

In this example, the angle of incidence is 14.5°, therefore, the scattered light at 14.5° scattering angle should be disregarded because 14.5° scattering angle is the angle of reflection.

The scattering intensity diagram of $s_{11}$ is omitted in both FIG. 7 and FIG. 8, this is due to the normalized denominator is $s_{11}$, that is, $$s_{ij}^* = \frac{s_{ij}}{s_{11}}, \; i = 1 \text{ to } 4, j = 1 \text{ to } 4.$$

The normalized elements, $s_{12}^*$ and $s_{34}^*$, are chosen, this is because they are more sensitive to the thickness of the film in FIG. 7 and FIG. 8. From the scattering intensity diagrams in both FIG. 7 and FIG. 8, the corresponding scattered angle of the scattered beam having maximum intensity variation around the reflecting angle, i.e. 14.5° in this example. Therefore, the normalized elements, $s_{12}^*$, $s_{34}^*$ and the scattered angle 12° are chosen. The selection of 12° is not unique, those scattered angles around the angle of reflection such as 10°, 11° or 16°, 19° could also be chosen instead of 12°.

It is to be understood that the normalized elements having greater sensitivity to the thickness of the film are chosen depend on what kind of film be used. Similarly, the range of the scattered angle of the scattered beam having maximum intensity variation is chosen also depend on what kind of film be used. Different kinds of films will have different choices of the normalized elements and the scattered angle.

The reasons for using the normalized elements, $s_{ij}^*$, instead of the elements, $s_{ij}$, are:

1. The intensity of the incident beam, $I_o$, is of no important.
2. The effect of the surface reflection of the linear polarized mirror and the phase delay plate can also be neglected.
3. The data of the normalized elements, $s_{ij}^*$, are more easily processed, since their values are ranged between $+1$ and $-1$, but for the unnormalized elements, $s_{ij}$, their values ranged several orders of magnitude.

Determination of the Film Thickness

Figure 10:
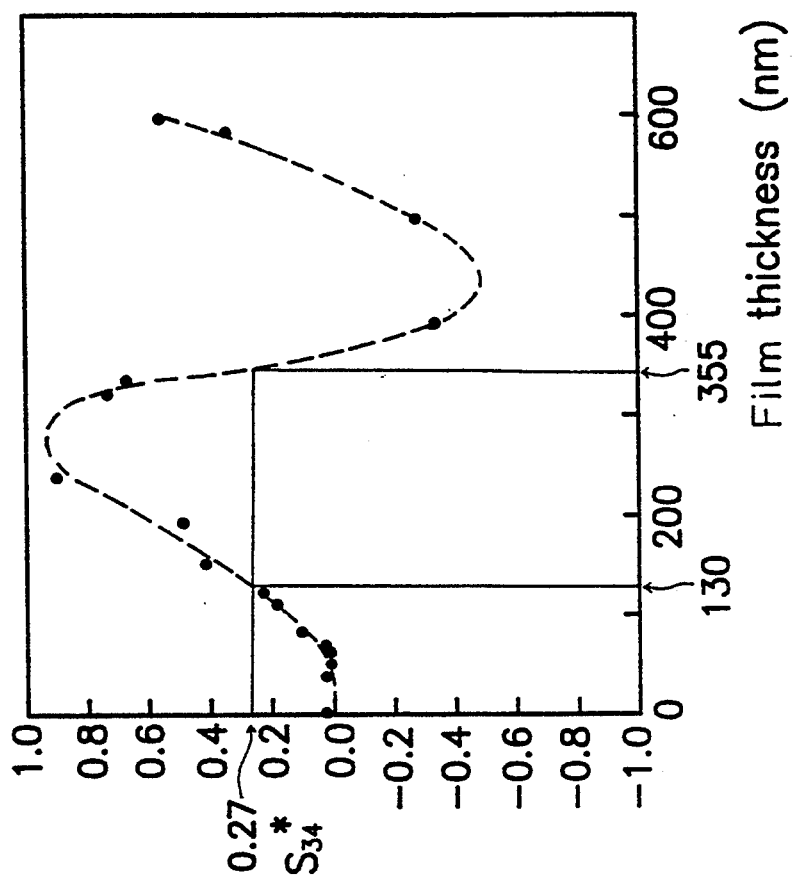
FIG. 10 depict a relation diagram between $s_{34}^*$ and $SiO_x$ film thickness.
Figure 9:
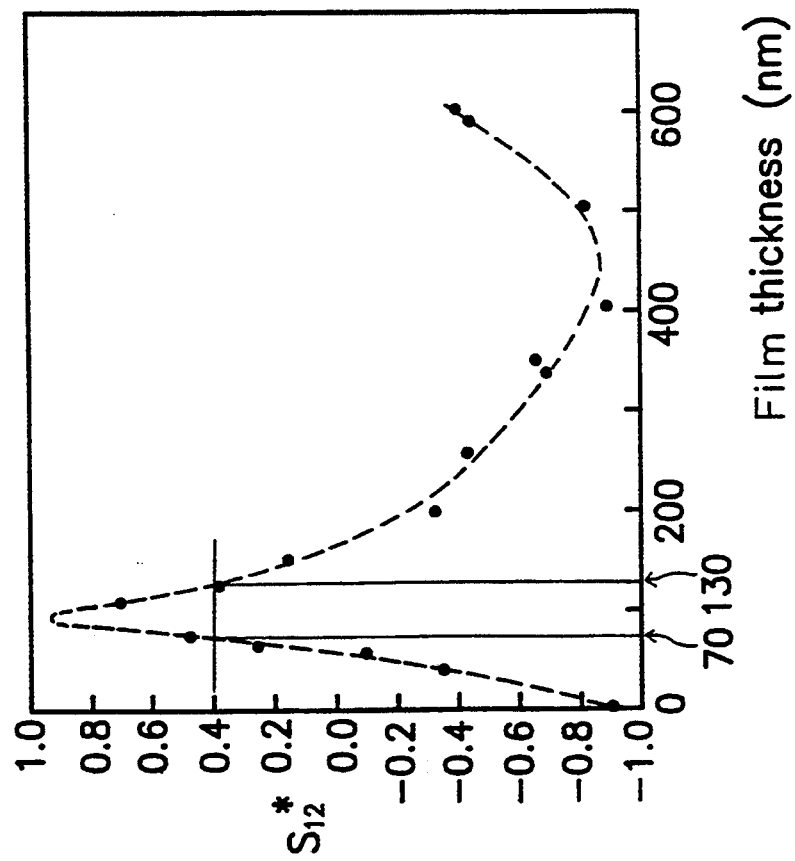
FIG. 9 depicts a relation diagram between $s_{12}^*$ and $SiO_x$ film thickness.

After choosing the normalized elements, $s_{12}^*$, $s_{34}^*$ as the normalized elements having greater sensitivity to the thickness of the film and the scattered angle 12° as the corresponding scattered angle of the scattered beam having maximum intensity variation, the relation diagrams between the normalized elements, $s_{12}^*$, $s_{34}^*$, and the $SiO_x$ film thickness are obtained in FIG. 9 and FIG. 10 respectively, and all the relation diagrams are obtained under the scattered angle 12°. The thicknesses of the films in FIG. 9 and FIG. 10 for this example are measured by using of ellipsometer.

For an unknown thickness of the same $SiO_x$ film, its value of normalized element, $s_{12}^*$, is measured to be 0.4 for example. Then its thicknesses are determined to be 70 nm or 130 nm corresponding to the relation diagram in FIG. 9. Similarly, the value of the normalized element, $s_{34}^*$, of the unknown thickness $SiO_x$ film is measured to be 0.27. Then its thicknesses are determined to be 130 nm or 355 nm corresponding to the relation diagram in FIG. 10. Finally, the thickness of the unknown thickness $SiO_x$ film is determined by choosing their common thickness, that is 130 nm.

While the invention has been described in terms of what are presently considered to be the most practical and preferred embodiments, it is to be understood that the present invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A method for measuring the thickness of a film coated on a partial portion of a substrate, comprising the following steps of:

(a) locating the origin of a X,Y,Z-coordinate on the surface of said substrate coated with said film, the normal direction of the surface of said substrate coated with said film being defined as the X-axis, the direction parallel to the surface of said substrate coated with said film being defined as the Y-axis, said film having a straight line edge on the Z-axis of the surface of said substrate coated with said film;

(b) generating a fixed polarization state input beam striking the straight line edge of said film, the path of said fixed polarization state input beam being on an X-Y plane;

(c) detecting the intensity of a fixed polarization state beam scattered by said fixed polarization state input beam striking the straight line edge of said film within a predetermined angular range;

(d) adjusting the relative intensity of said fixed polarization state input beam and said fixed polarization state beam scattered by said fixed polarization state input beam striking the straight line edge of said film;

(e) obtaining a 4×4 matrix, S, that can transfer a 4×1 matrix, $S_i$, that represents the polarization state of said fixed polarization state input beam to a 4×1 matrix, $S_s$, that represents the polarization state of said fixed polarization state beam scattered by said fixed polarization state input beam striking the straight line edge of said film by using the Bickel-Bailey method, that is $$S_S = S \cdot S_i$$

where the dot, "·", represents multiplication, the 4×4 matrix, S, is named as "Mueller matrix" and is defined to be $$S = \begin{bmatrix} s_{11} & s_{12} & s_{13} & s_{14} \\ s_{21} & s_{22} & s_{23} & s_{24} \\ s_{31} & s_{32} & s_{33} & s_{34} \\ s_{41} & s_{42} & s_{43} & s_{44} \end{bmatrix};$$

(f) normalizing all the elements of the Mueller matrix, said normalized elements, $s_{ij}^*$, is defined as $$s_{ij}^* = \frac{s_{ij}}{s_{11}}, i = 1 \text{ to } 4, j = 1 \text{ to } 4;$$

(g) recording the corresponding scatter angle of said fixed polarization state beam scattered by said fixed polarization state input beam striking the straight line edge of said film having maximum intensity variation;

(h) obtaining the relation diagrams between said normalized elements, $s_{12}^*$, $s_{21}^*$, $s_{22}^*$, $s_{33}^*$, $s_{34}^*$, $s_{43}^*$, $s_{44}^*$ and the thickness of said film respectively by repeating said step (a) to said step (f) with different predetermined thicknesses of said film, and all the relation diagrams are obtained under the corresponding scattered angle of said fixed polarization state beam scattered by said fixed polarization state input beam striking the straight line edge of said film having maximum intensity variation;

(i) choosing the relation diagrams in said step (h) that said normalized elements, $s_{12}^*$, $s_{21}^*$, $s_{22}^*$, $s_{33}^*$, $s_{34}^*$, $s_{43}^*$, $s_{44}^*$ have greater sensitivity to the thickness of said film;

(j) repeating said step (a) to said step (f) with an unknown thickness of said film, and obtaining the values of normalized elements, $s_{12}^*$, $s_{21}^*$, $s_{22}^*$, $s_{33}^*$, $s_{34}^*$, $s_{43}^*$, $s_{44}^*$ of said film of unknown thickness;

(k) obtaining the thicknesses of said film of unknown thickness from the relation diagrams obtained in said step (i) corresponding to the relation diagrams by using the values of said normalized elements, $s_{12}^*$, $s_{21}^*$, $s_{22}^*$, $s_{33}^*$, $s_{34}^*$, $s_{43}^*$, $s_{44}^*$ in said step (j) respectively; and (l) determining the thickness of said film of unknown thickness by choosing the common thickness among the relation diagrams in said step (k).

2. A polarized-light scatterometer for measuring the thickness of a film coated on the partial of a substrate, comprising:

(a) means for locating the origin of a X,Y,Z-coordinate on the surface of said substrate coated with said film, the normal direction of the surface of said substrate coated with said film is defined as the X-axis, the direction parallel to the surface of said substrate coated with said film is defined as the Y-axis, said film having a straight line edge on the Z-axis of the surface of said substrate coated with said film;

(b) means for generating a fixed polarization state input beam striking the straight line edge of said film, the path of said fixed polarization state input beam being on an X-Y plane;

(c) means for detecting the intensity of a fixed polarization state beam scattered by said fixed polarization state input beam striking the straight line edge of said film within a predetermined angular range;

(d) means for rotating said detecting means about said Z-axis within said predetermined angular range;

(e) means for adjusting the relative intensity of said fixed polarization state input beam and said fixed polarization state beam scattered by said fixed polarization state input beam striking the straight line edge of said film;

(f) means for obtaining a 4×4 matrix, S, that can transfer a 4×1 matrix, $S_i$, that represents the polarization state of said fixed polarization state input beam to a 4×1 matrix, $S_s$, that represents the polarization state of said fixed polarization state beam scattered by said fixed polarization state input beam striking the straight line edge of said film by using the Bickel-Bailey method, that is $$S_S = S \cdot S_i$$

where the dot, "·", represents multiplication, the 4×4 matrix, S, is named as "Mueller matrix" and is defined to be $$S = \begin{bmatrix} s_{11} & s_{12} & s_{13} & s_{14} \\ s_{21} & s_{22} & s_{23} & s_{24} \\ s_{31} & s_{32} & s_{33} & s_{34} \\ s_{41} & s_{42} & s_{43} & s_{44} \end{bmatrix};$$

(g) means for normalizing all the elements of the Mueller matrix, said normalized elements, $s_{ij}^*$, being defined as $$s_{ij}^* = \frac{s_{ij}}{s_{11}}, i = 1 \text{ to } 4, j = 1 \text{ to } 4;$$

(h) means for recording the corresponding scatter angle of said fixed polarization state beam scattered by said fixed polarization state input beam striking the straight line edge of said film having maximum intensity variation;

(i) means for obtaining the relation diagrams between said normalized elements, $s_{12}^*$, $s_{21}^*$, $s_{22}^*$, $s_{33}^*$, $s_{34}^*$, $s_{43}^*$, $s_{44}^*$ and the thickness of said film respectively by repeating said step (a) to said step (g) with different predetermined thicknesses of said film, and all the relation diagrams are obtained under the corresponding scatter angle of said fixed polarization state beam scattered by said fixed polarization state input beam striking the straight line edge of said film having maximum intensity variation;

(j) means for choosing the relation diagrams in said step (i) that said normalized elements, $s_{12}^*$, $s_{21}^*$, $s_{22}^*$, $s_{33}^*$, $s_{34}^*$, $s_{43}^*$, $s_{44}^*$ have greater sensitivity to the thickness of said film;

(k) means for repeating said step (a) to said step (g) with an unknown thickness of said film, and obtaining the values of normalized elements, $s_{12}^*$, $s_{21}^*$, $s_{22}^*$, $s_{33}^*$, $s_{34}^*$, $s_{43}^*$, $s_{44}^*$ of said film of unknown thickness;

(l) means for obtaining the thicknesses of said film of unknown thickness from the relation diagrams obtained in said step (j) corresponding to the relation diagrams by using the values of said normalized elements, $s_{12}^*$, $s_{21}^*$, $s_{22}^*$, $s_{33}^*$, $s_{34}^*$, $s_{43}^*$, $s_{44}^*$ in said step (k) respectively; and (m) means for determining the thickness of said film of unknown thickness by choosing the common thickness among the relation diagrams in said step (l).

* * * * *

UNITED STATES PATENT AND TRADEMARK OFFICE
CERTIFICATE OF CORRECTION

PATENT NO. : 5,381,233
DATED : January 10, 1995
INVENTOR(S) : Shiuh Chao, et al.

It is certified that error appears in the above-indentified patent and that said Letters Patent is hereby corrected as shown below:

On the title page:

Item [73] Assignee: add

Industrial Technology Research Institute

Hsinchu, Taiwan, R.O.C.

Signed and Sealed this

Twenty-ninth Day of April, 1997

Attest:

BRUCE LEHMAN

Attesting Officer

Commissioner of Patents and Trademarks